(12) United States Patent
Satou et al.

(10) Patent No.: US 7,497,109 B2
(45) Date of Patent: Mar. 3, 2009

(54) STRUCTURE OF GAS SENSOR DESIGNED TO MINIMIZE DAMAGE TO PORCELAIN INSULATORS

(75) Inventors: Yasuyuki Satou, Kasugai (JP); Seiji Maeda, Suzuka (JP)

(73) Assignee: Denso Corporation, Kariya (JP)

( * ) Notice: Subject to any disclaimer, the term of this patent is extended or adjusted under 35 U.S.C. 154(b) by 334 days.

(21) Appl. No.: 11/387,054

(22) Filed: Mar. 23, 2006

(65) Prior Publication Data

US 2006/0213254 A1 Sep. 28, 2006

(30) Foreign Application Priority Data

Mar. 23, 2005 (JP) ............................. 2005-083621
Nov. 4, 2005 (JP) ............................. 2005-320941

(51) Int. Cl.
*G01N 7/00* (2006.01)
(52) U.S. Cl. .................................................. 73/31.05
(58) Field of Classification Search .................. 73/31.05
See application file for complete search history.

(56) References Cited

U.S. PATENT DOCUMENTS

| | | | |
|---|---|---|---|
| 6,418,777 B1 | 7/2002 | Noda et al. | |
| 6,550,309 B1 | 4/2003 | Noda et al. | |
| 6,615,641 B2 | 9/2003 | Kojima | |
| 6,708,551 B2 * | 3/2004 | Kojima | ........................ 73/31.05 |
| 7,178,382 B2 * | 2/2007 | Noda et al. | ................. 73/31.05 |

FOREIGN PATENT DOCUMENTS

| | | |
|---|---|---|
| JP | H11-242013 | 9/1999 |
| JP | 2001-343355 | 12/2001 |

* cited by examiner

*Primary Examiner*—Daniel S Larkin
*Assistant Examiner*—Rodney T Frank
(74) *Attorney, Agent, or Firm*—Nixon & Vanderhye PC

(57) ABSTRACT

A gas sensor made up of a sensor element and a first and a second hollow cylindrical porcelain insulators covering the sensor element. The first porcelain insulator is laid on the second porcelain insulator in alignment within a body of the gas sensor. A base end surface of the first porcelain insulator is placed in abutment with a top end surface of the second porcelain insulator. At least one of the base end surface of the top end surface has a ground flat area which forms an interface between the first and second porcelain insulators without micro-contacts resulting in concentration of local stress which would lead to breakage of the first or second porcelain insulator when subjected to physical loads.

8 Claims, 13 Drawing Sheets

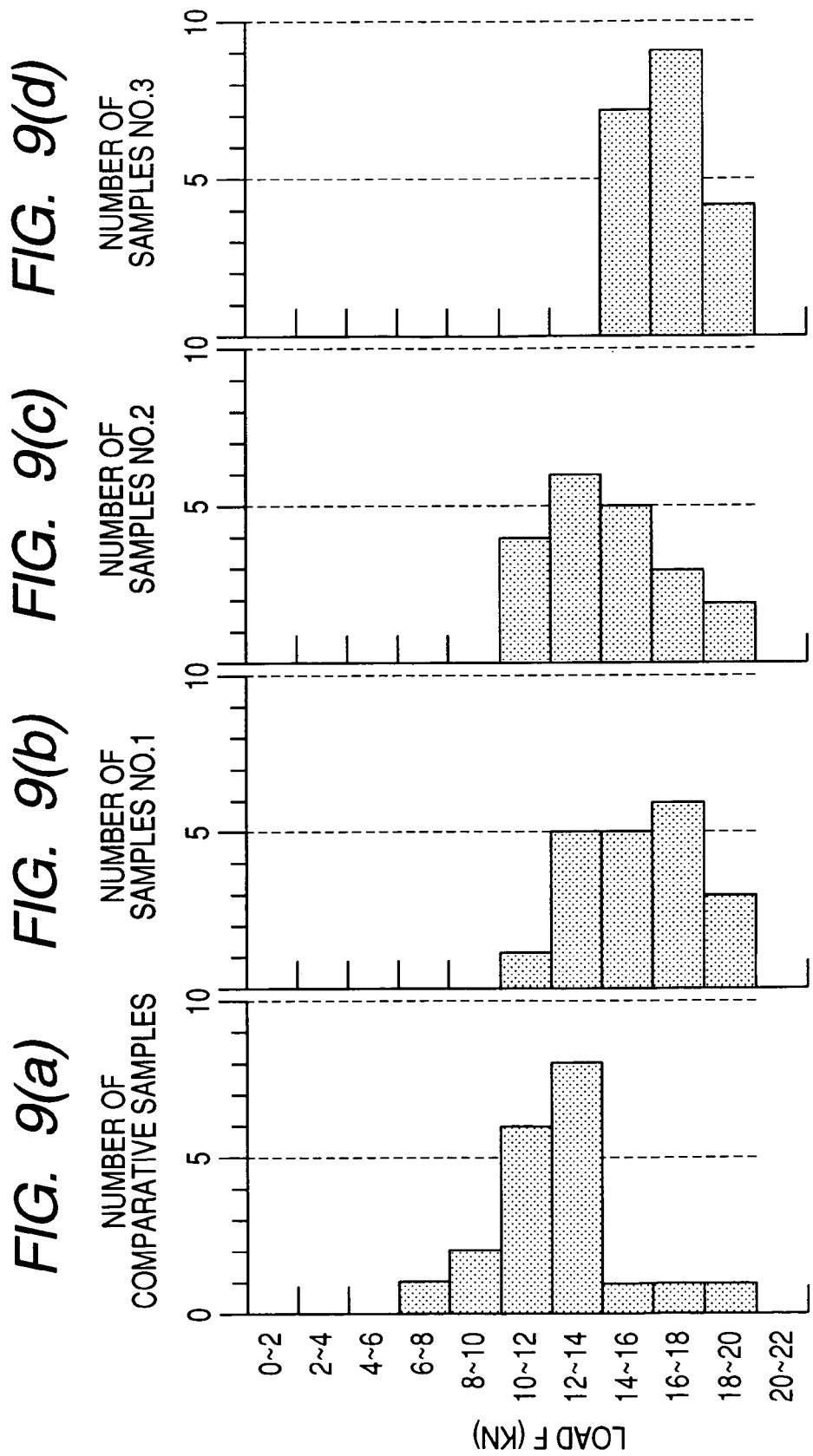

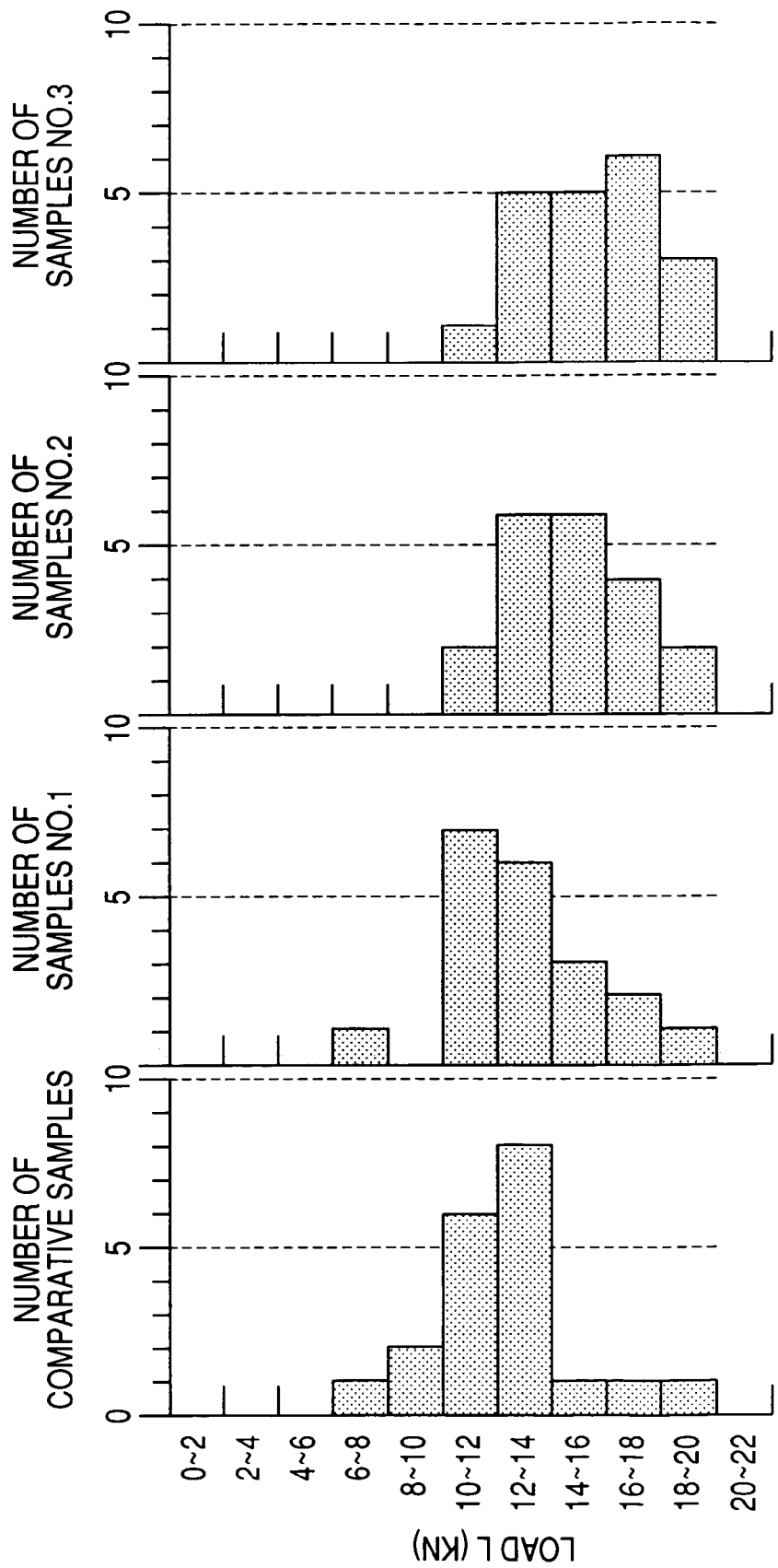

STRUCTURE OF GAS SENSOR DESIGNED TO MINIMIZE DAMAGE TO PORCELAIN INSULATORS

CROSS REFERENCE TO RELATED DOCUMENT

The present application claims the benefits of Japanese Patent Application No. 2005-83621 filed on Mar. 23, 2005 and Japanese Patent Application No. 2005-320941 filed on Nov. 4, 2005 disclosures of which are incorporated herein by reference.

BACKGROUND OF THE INVENTION

1. Technical Field of the Invention

The present invention relates generally to a gas sensor which may be installed in an exhaust system of an internal combustion engine for air-fuel ratio control, and more particularly to an improved structure of a gas sensor designed to ensure a desired mechanical strength of built-in porcelain insulators in withstanding applied physical loads.

2. Background Art

Japanese patent First Publication No. 2001-343355 discloses a conventional gas sensor 9, as illustrated in FIG. 17, which is used in burning control of an internal combustion engine. The gas sensor 9 includes a housing 90, a first porcelain insulator 91, a second porcelain insulator 92, and a sensor element 8. The first porcelain insulator 91 is retained in the housing 90. The sensor element 8 is inserted into the first porcelain insulator 91. The second porcelain insulator 92 is disposed in abutment with a base end surface 910 of the first porcelain insulator 91.

The first porcelain insulator 91 and the second porcelain insulator 92 are typically made of an insulating ceramic material. When burned or fired, the ceramic material is usually subjected to variation in local shrinkage due to a variation in density of the ceramic material occurring during production thereof or quantity of heat the ceramic material undergoes during the firing thereof, thus resulting in micro undulations on the base end surface 910 of the first porcelain insulator 91 and a top end surface 920 of the second porcelain insulator 92.

The undulations may result in undesirable shifting of a contact area 93 between the first porcelain insulator 91 and the second porcelain insulator 92 from an annular gasket 94 through which the first porcelain insulator 91 is seated on the housing 90 in a direction perpendicular to the length of the gas sensor 9. This causes the bending stress to act on the first porcelain insulator 91 which would lead to breakage of the first porcelain insulator 91.

In order to avoid the above problem, the second porcelain insulator 92 is aligned to the first porcelain insulator 91 so that the contact area 93 is located within a region T defined by projecting the profile of the annular gasket 94 disposed on an inner shoulder 900 of the housing 90 onto the base end surface 910 of the first porcelain insulator 91 in an axial direction of the gas sensor 9, thereby holding the contact area 93 from being shifted horizontally to minimize the bending stress which would result in the breakage of the first porcelain insulator 91.

The above structure, however, still has the problem in that within the contact area 93, the first and second porcelain insulators 91 and 92 are in abutment of curves surfaces of tops of the undulations to each other through which the first porcelain insulator 91 and the second porcelain insulator 92 receive the load from each other, which may result in the breakage thereof.

Usually, the ceramic material has many inherent defects such as pores or micro cracks in the surface thereof. Such defects, therefore, exist in the base end surface 910 of the first porcelain insulator 91 and the top end surface 920 of the second porcelain insulator 92, thus leading to a greater concern about the breakage occurring when the first and second porcelain insulators 91 and 92 are subjected to the physical load.

SUMMARY OF THE INVENTION

It is therefore a principal object of the invention to avoid the disadvantages of the prior art.

It is another object of the invention to provide an improved structure of a gas sensor which is designed to avoid breakage of porcelain insulators installed in a housing of the gas sensor According to one aspect of the invention, there is provided a gas sensor which may be installed in an exhaust system of an automotive internal combustion engine to measure the concentration of a selected component of emissions for use in burning control of the engine. The gas sensor comprises: (a) a hollow cylindrical housing; (b) a sensor element including a sensing portion and a base portion, the sensing portion working to produce a signal as a function of concentration of a target component of gases; (c) a first porcelain insulator having a top end surface and a base end surface opposed to the top end surface, the first porcelain insulator being installed in the housing and through and having the sensor element pass therethrough to expose the sensing portion to the gases outside the top end surface of the housing; a second porcelain insulator having a top end surface and a base end surface opposed to the top end surface, the second porcelain insulator being aligned with the first porcelain insulator in abutment of the top end surface thereof with the base end surface of the first porcelain insulator; and (e) a ground flat area formed on at least one of the base end surface of the first porcelain insulator and the top end surface of the second porcelain insulator to define an area of contact between the base end surface of the first porcelain insulator and the top end surface of the second porcelain insulator. Specifically, the base end surface of the first porcelain insulator and the top end surface of the second porcelain insulator are placed in abutment with each other through the ground flat surface. The base end surface of the first porcelain insulator and the top end surface of the second porcelain insulator, therefore, do not have micro-contacts therebetween, thereby minimizing the concentration of local stress on the base end surface of the first porcelain insulator and the top end surface of the second porcelain insulator to avoid breakage of the first porcelain insulator or the second porcelain insulator.

In the preferred mode of the invention, it is advisable that each of the base end surface of the first porcelain insulator and the top end surface of the second porcelain insulator have the ground flat area.

Each of the first and second porcelain insulator is made of a cylindrical member. The ground flat area occupies a distance of 0.5 mm or more on the one of the base end surface of the first porcelain insulator and the top end surface of the second porcelain insulator in a radius direction of the one.

The ground flat area is so formed that an amplitude of an envelope curve defined by connecting peaks of undulations in a sequence of small zones to which a surface of the ground flat area is divided in unit of 0.5 mm in a selected direction lies within a range of 5 µm or less. This minimizes the concentration of local stress on the base end surface of the first porcelain insulator and the top end surface of the second porcelain insulator to avoid breakage of the first porcelain insulator or the second porcelain insulator.

The first porcelain insulator has a recess formed in the base end surface thereof. The second porcelain insulator has a protrusion formed on the top end surface thereof. The first and second porcelain insulators are placed in engagement of the recess in the base end surface of the first porcelain insulator with the protrusion on the top end surface of the second porcelain insulator. Specifically, the recess and the protrusion function as a positioning mechanism to ensure the alignment of the first and second porcelain insulators. The first and second porcelain insulators are made of ceramic material. The formation of the recess and protrusion, therefore, would result in a variation in grain density of the ceramic material around the recess and the protrusion during molding thereof. When burned or fired, the ceramic material is subjected to variation in local shrinkage due to the variation in density or quantity of heat the ceramic material undergoes, thus resulting in micro undulations on and many defects such as pore or micro cracks in the base end surface of the first porcelain insulator and the top end surface of the second porcelain insulator. This leads to a greater concern about the breakage occurring when the first and second porcelain insulators are subjected to physical loads. Accordingly, the formation of the ground area on the at least one of the base end surface of the first porcelain insulator and the top end surface of the second porcelain insulator is very useful for the structure of the gas sensor in which the recess is formed in the base end surface of the first porcelain insulator, and the protrusion is formed on the top end surface of the second porcelain insulator.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 4($b$) is a plan view which shows a top end surface of a second porcelain insulator;

FIG. 6($b$) is a partially enlarged sectional view which shows an area of contact between a ground area formed on an end surface of a first porcelain insulator and undulations on an end surface of a second porcelain insulator of a gas sensor of the second embodiment of the invention;

FIG. 7($b$) is a partially enlarged sectional view which shows an area of contact between end surfaces of a first and a second porcelain insulators of a gas sensor of the second embodiment of the invention;

FIGS. 9($a$), 9($b$), 9($c$), and 9($d$) are graphs representing results of tests performed on the gas sensor samples using the test device of FIG. 8;

FIGS. 11($a$), 11($b$), 11($c$), and 11($d$) are graphs representing results of tests performed on the gas sensor samples, as illustrated in FIGS. 10($a$), 10($b$), and 10($c$);

FIG. 12($b$) is a plane view which represents directions in which the flatness of a top end surface of a second porcelain insulator was measured experimentally;

FIG. 13($b$) is a graph which show the profile of a base end surface of a first porcelain insulator after ground, as measured along the line A-A' in FIG. 12($a$);

FIG. 14($b$) is a graph which shows the profile of a base end surface of a first porcelain insulator after ground, as measured along the line B-B' in FIG. 12($a$);

FIG. 15($b$) is a graph which shows the profile of a top end surface of a second porcelain insulator after ground, as measured along the line C-C' in FIG. 12($b$);

FIG. 16($b$) is a graph which shows the profile of a top end surface of a second porcelain insulator after ground, as measured along the line D-D' in FIG. 12($b$)

DESCRIPTION OF THE PREFERRED EMBODIMENTS

Figure 1:
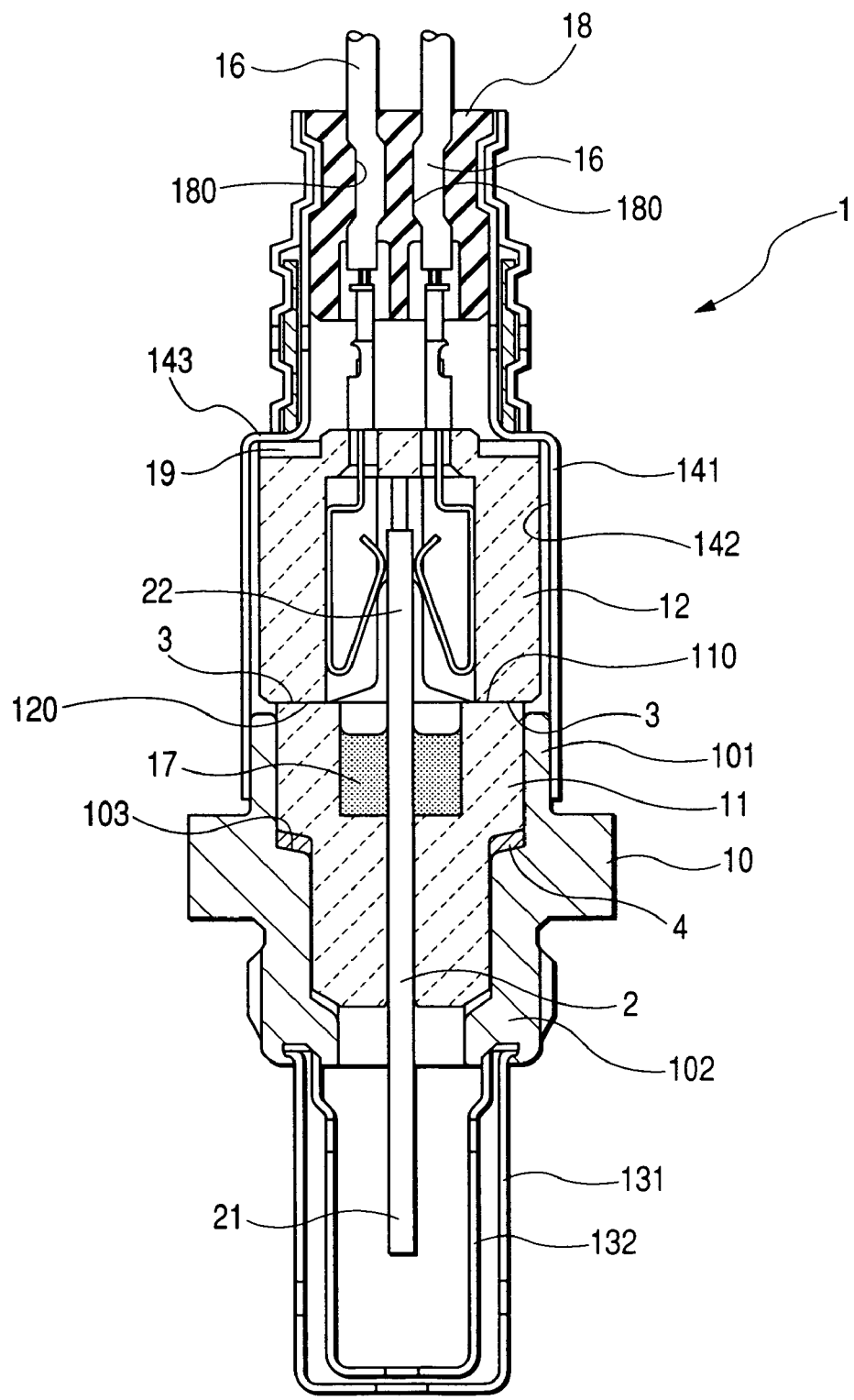
FIG. 1 is a longitudinal sectional view which shows a gas sensor according to the first embodiment of the invention.

Referring to the drawings, wherein like reference numbers refer to like parts in several views, particularly to FIGS. 1 to 5, there is shown a gas sensor 1 according to the first embodiment of the invention which may be employed in a burning control system for automotive vehicles to measure concentrations of components such as NOx, CO, HC, and $O_2$ contained in exhaust gasses of an internal combustion engine.

The gas sensor 1 will be described below, as an example, as being installed in an exhaust system of an automotive engine to measure the concentration of oxygen ($O_2$) contained in emissions for use in burning control of the engine.

The gas sensor 1 generally includes a sensor element 2, a first hollow cylindrical porcelain insulator 11, a second hollow cylindrical porcelain insulator 12, and a hollow cylindrical housing 10, an air cover 141, and a protective cover assembly made up of outer and inner covers 131 and 132. The sensor element 2 is made of a laminated plate which consists essentially of a solid-electrolyte layer(s), an insulating layer(s), and a heater. The insulating layer(s) may alternatively be omitted. The sensor element 2 has a given length made up of a sensing portion 21 and a base portion 22. For example, U.S. Pat. No. 5,573,650, issued on Nov. 12, 1996 to Fukaya et al. teaches a typical laminated sensor element, disclosure of which is incorporated herein by reference.

The first porcelain insulator 11 and the second porcelain insulator 12 are made of ceramic material such as $Al_2O_3$. The first porcelain insulator 11 is fitted within the housing 10 and holds therein the sensor element 2. The second porcelain insulator 12 is aligned with the first porcelain insulator 11 in abutment of a top end surface 120 thereof with a base end surface 110 of the first porcelain insulator 11 and surrounds the base portion of the sensor element 2. The air cover 141 is installed at an end thereof on the housing 10 to cover the second porcelain insulator 12. The protective cover assembly has a double-walled structure made up of the outer and inner covers 131 and 132 and is installed and staked in an annular groove formed in an and of the housing 10 to cover the sensing portion of the sensor element 2.

Figure 2:
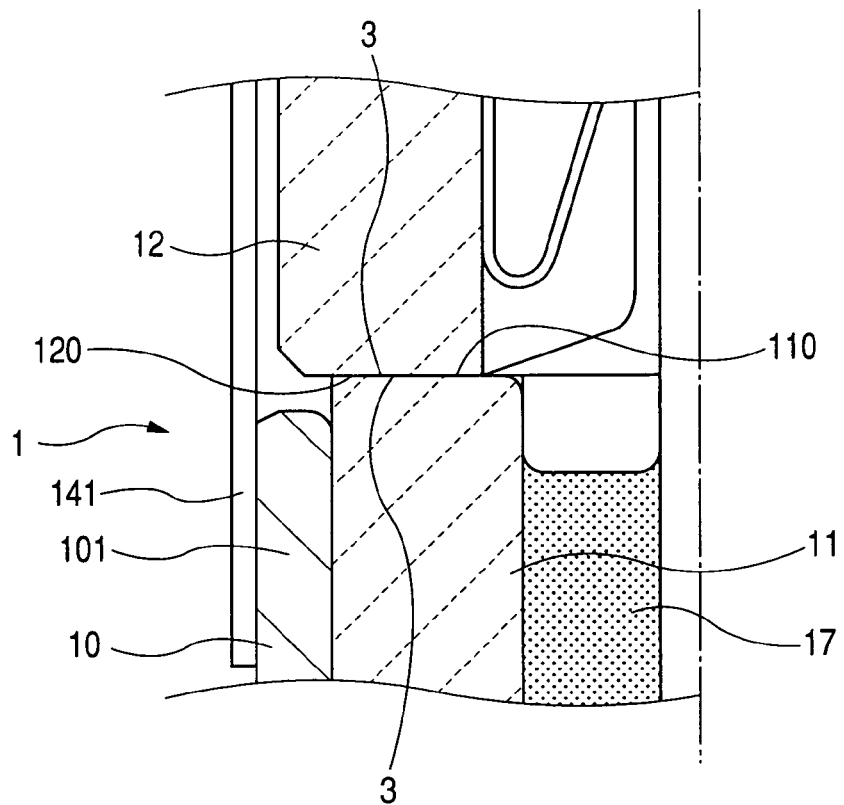
FIG. 2 is a partial sectional view which shows abutment of a first and a second porcelain insulator in the gas sensor of FIG. 1.
Figure 3:
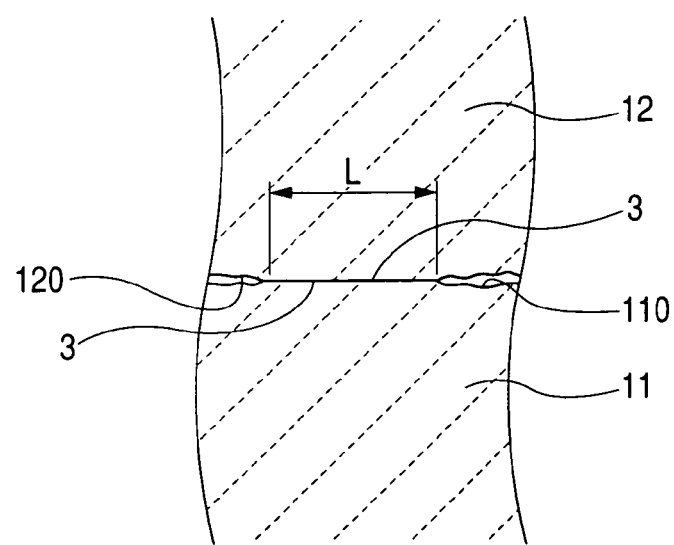
FIG. 3 is a partially enlarged sectional view which shows a desired range within which ground areas are to be formed on the first and second porcelain insulators in FIG. 2.

Each of the base end surface 110 of the first porcelain insulator 11 and the top end surface 120 of the second porcelain insulator 12, as clearly illustrated in FIGS. 1 to 3, has a ground flat area 3 which extends perpendicular to a longitudinal center line of the gas sensor 1 (i.e., the first and second porcelain insulators 11 and 12). The base end surface 110 of the first porcelain insulator 11 and the top end surface 120 of the second porcelain insulator 12 are placed in abutment with each other at the ground flat areas 3.

Figure 4A:
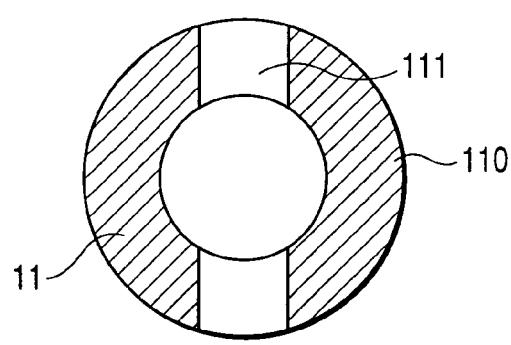
FIG. 4($a$) is a plan view which shows a base end surface of a first porcelain insulator.
Figure 5:
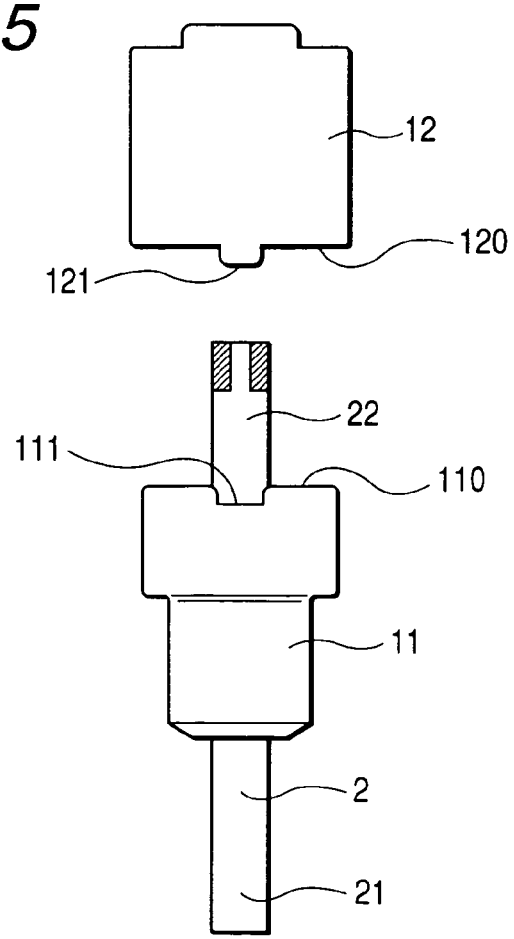
FIG. 5 is an exploded front view which shows a sensor element, a first porcelain insulator, and a second porcelain insulator to be assembled in the gas sensor of FIG. 1.

The first porcelain insulator 11, as clearly shown in FIGS. 4(a) and 5, has recesses 111 formed in the base end surface 110 which are aligned to each other horizontally. The second porcelain insulator 12 has formed on the top end surface 120 protrusions 121 which are to be fitted in the recesses 111 of the first porcelain insulator 11. Specifically, the recesses 111 and the protrusions 121 function as a positioning mechanism to align the first and second porcelain insulators 11 and 12 with the longitudinal center line of the gas sensor 1.

Figure 4B:
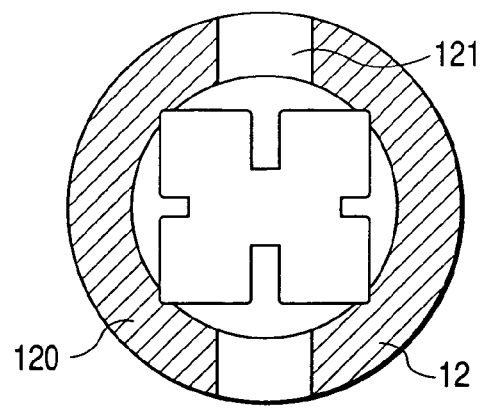

The first porcelain insulator 11 and the second porcelain insulator 12 are joined to each other so that the base end surface 110 and the top end surface 120 are placed in abutment with each other, and the protrusions 121 are fit in the recesses 111. Specifically, a hatched area of the first porcelain insulator 11, as illustrated in FIG. 4(a), that is the based end surface 110 except the recesses 110 forms an area of contact with a hatched area of the second porcelain insulator 12, as illustrated in FIG. 4(b), that is the top end surface 120 except the protrusions 121. The ground areas 3 of the first and second porcelain insulators 11 and 12 are formed in the hatched areas, respectively.

The ground areas 3 are preferably so formed as to occupy the wholes of the hatched areas of the first and second porcelain insulators 11 and 12, but may, as illustrated in FIG. 3, occupy only portions of the base end surface 110 and the top end surface 120, respectively. The base end surface 110 of the first porcelain insulator 11 and the top end surface 120 of the second porcelain insulator 12 each have a diameter of, for example, 15 mm or 17 mm. The width L of each of the ground areas 3 in a radius direction of the gas sensor 1 is preferably 0.5 mm or more. The length of the ground areas 3 in a circumferential direction of the first and second porcelain insulators 11 and 12 is much greater than the width L.

Each of the ground areas 3 is so formed that the amplitude of an envelope curve defined by connecting peaks of undulations in a sequence of small zones to which the surface of the ground area 3 is subdivided in unit of 0.5 mm in any selected direction lies within a range of 5 μm or less.

Referring back to FIG. 1, the gas sensor 1, as described above, includes the air cover 141 and the protective cover assembly made up of outer and inner covers 131 and 132. The base portion 22 of the sensor element 2 is retained inside the second porcelain insulator 12. The sensing portion 21 is exposed to a gas chamber defined by the outer and inner covers 131 and 132.

The first porcelain insulator 11 is retained within the housing 10 hermetically and holds therein a middle portion of the sensor element 2 through a glass sealing member 17.

An insulating holder 18 made of a rubber bush is disposed inside a small-diameter portion of the air cover 141. The insulating holder 18 has formed therein four through holes 180 (only two are shown for the brevity of illustration) into which the four leads 16 are inserted, respectively.

The second porcelain insulator 12 is retained between the base end surface 110 of the first porcelain insulator 111 and a shoulder 143 of the air cover 141. A disc spring 19 is disposed between the shoulder 143 of the air cover 141 and the end of the second porcelain insulator 12 to press the second porcelain insulator 12 against the first porcelain insulator 11.

The first porcelain insulator is retained on an annular shoulder 103 formed on an inner wall of the housing 10 through an annular gasket 4.

When the gas sensor 1 is installed in the exhaust pipe of the automotive engine, the sensing portion 21 of the sensor element 2 is exposed to and reacts with exhaust gasses electrochemically. The sensor element 2 has electrodes affixed to the sensing portion 21 which produce an electrical current through the electrochemical reaction as a function of concentration of oxygen contained in the exhaust gasses and output it outside the gas sensor 1 through the leads 16. This operation of the gas sensor 1 is a typical one, and explanation thereof in detail will be omitted here.

The ground areas 3 of the first and second insulator porcelain 11 and 12 may be formed using a lapping machine or a grinding machine.

The base end surface 110 of the first porcelain insulator 11 and the top end surface 120 of the second porcelain insulator 12 are, as described above, placed in abutment of the ground areas 3 with each other. The base end surface 110 and the top end surface 120, therefore, do not have micro-contacts, as in the conventional structure discussed in the introductory part of this application, between undulations on the base end surface 110 and the top end surface 120, thereby minimizing the concentration of local stress on the base end surface 110 and the top end surface 120 to avoid breakage of the first porcelain insulator 11 or the second porcelain insulator 12.

The ground areas 3 of the first and second porcelain insulators 11 and 12 are flat and, thus, form a wide contact interface between the base end surface 110 and the top end surface 120, thereby resulting in distribution of physical loads over the whole of the contact interface, which enhances the avoidance of breakage of the first porcelain insulator 11 or the second porcelain insulator 12.

Usually, the ceramic material of the first and second porcelain insulators 11 and 12 has many inherent defects such as pores or micro cracks in the surface thereof. Most of such defects appear at the base end surface 110 of the first porcelain insulator 11 and the top end surface 120 of the second porcelain insulator 12, thus leading to a greater concern about the breakage occurring when the first and second porcelain insulators 11 and 12 are subjected to the physical load. The formation of the ground area 3 results in elimination of such defects, thus minimizing the possibility of breakage of the first porcelain insulator 11.

The first and second porcelain insulators 11 and 12 are, as already described, made of ceramic material, The formation of the recesses 111 in the first porcelain insulator 11 and the protrusions 121 on the second porcelain insulator 12, therefore, would result in a variation in grain density of the ceramic material around the recesses 111 and the protrusions 121 during molding thereof. When burned or fired, the ceramic material is subjected to variation in local shrinkage due to the variation in grain density or quantity of heat the ceramic material undergoes, thus resulting in micro undulations on and many defects such as pore or micro cracks in the base end surface 110 of the first porcelain insulator 11 and the top end surface 120 of the second porcelain insulator 12. This leads to a greater concern about the breakage occurring when the first and second porcelain insulators 11 and 12 are subjected to physical loads. Accordingly, the formation of the ground areas 3 is very useful for the gas sensor 1 equipped with the recesses 11 and the protrusions 121.

Figure 6A:
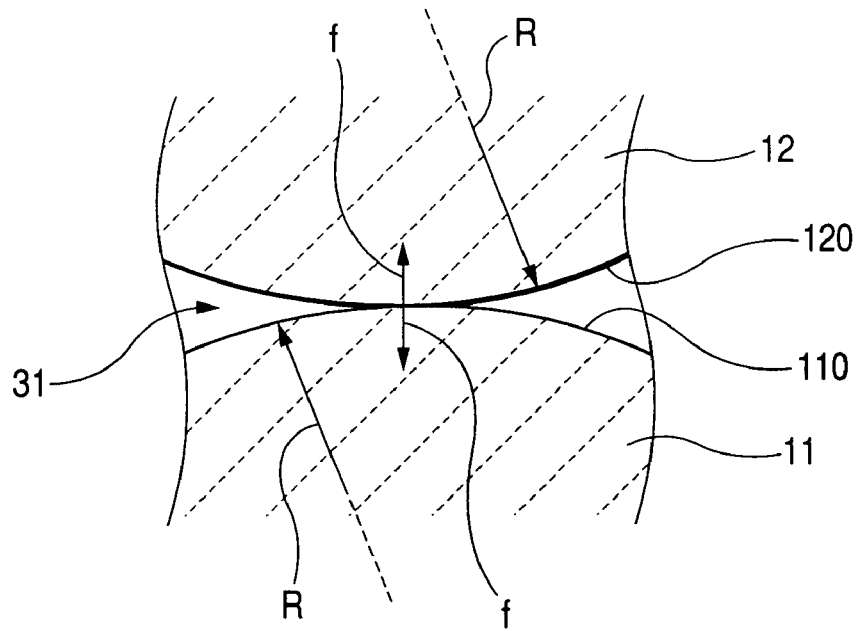
FIG. 6($a$) is a partially enlarged sectional view which shows an area of contact between undulations on end surfaces of a first and a second porcelain insulators of a gas sensor.
Figure 6B:
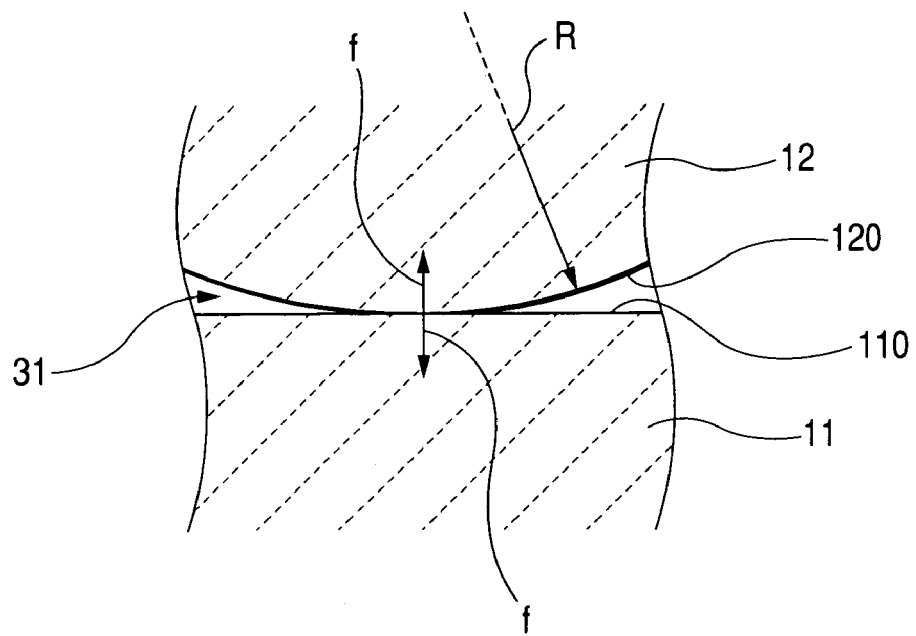
Figure 7A:
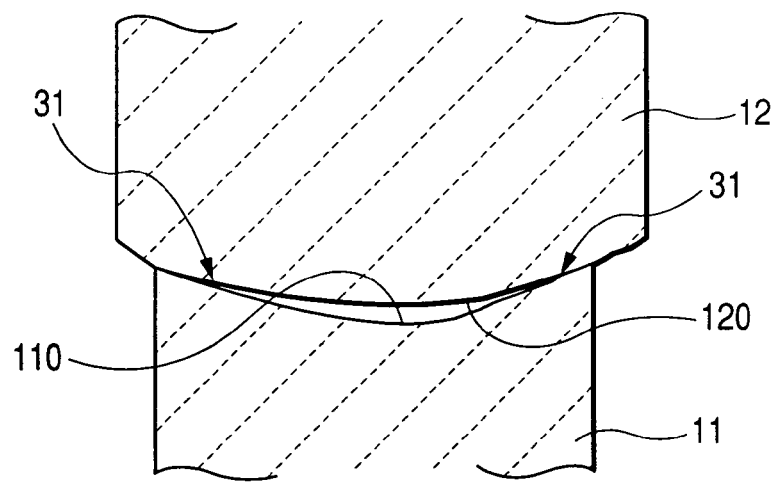
FIG. 7($a$) is a partially enlarged sectional view which shows an area of contact between end surfaces of a first and a second porcelain insulators of a conventional example of a gas sensor.
Figure 7B:
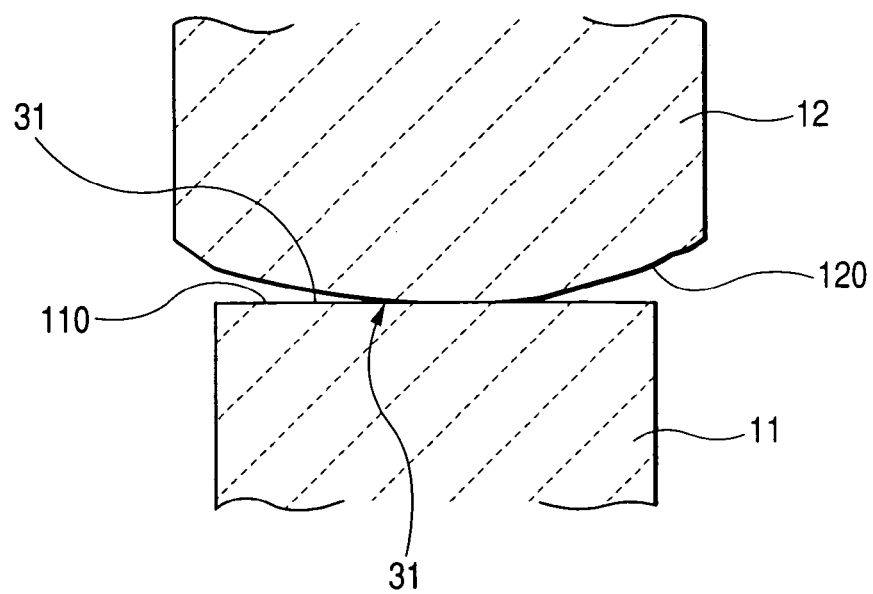

FIGS. 6(b) and 7(b) show the gas sensor 1 according to the second embodiment of the invention in which only the base end surface 110 of the first porcelain insulator 11 has the ground area 3. Other arrangements are identical with those in the first embodiment, and explanation thereof in detail will be omitted here.

The ground area 3 on the base end surface 110 of the first porcelain insulator 11, like the first embodiment, serves to minimize or eliminate micro-contact areas between the undulations on the base end surface 110 and the top end surface 120 of the second porcelain insulator 12, thereby minimizing the concentration of local stress on the first and second porcelain insulators 11 and 12 to avoid the breakage thereof.

The formation of the ground area 3 results in elimination of the inherent defects such as pores or micro cracks in the base end surface 110 of the first porcelain insulator 11, thus minimizing the possibility of breakage of the first porcelain insulator 11 due to such defects.

FIGS. 6(a) and 7(a) show examples where the base end surface 110 of the first porcelain insulator 11 and the top end surface 120 of the second porcelain insulator 12 are both not ground to be flat. The base end surface 110 and the top end surface 120, as described above, usually have micro undulations formed thereon. When tops of the undulations abut each other, the stress $P_0$ acting on the center of the contact area 31 is expressed by the following equation.

$$P_0^3 = 6/\pi^3 \times R^{-2} \times ((1-\nu^2)/E)^{-2} \times f \quad (1)$$

where R is a radius of curvature of the undulations if curved surfaces of all the undulations have the same curvature, $\nu$ is the Poisson's ratio, E is the Young's modulus, and f is the load acting on the first and second porcelain insulators 11 and 12.

Even in the case where a convex surface and a concave surface, as illustrated in FIG. 7(a), are viewed macroscopically as being in abutment with each other, the tops of the undulations, as viewed microscopically in FIG. 6(a), may be placed in abutment with each other.

When one of the base end surface 110 of the first porcelain insulator 11 and the top end surface 120 of the second porcelain insulator 12, e.g., the based end surface 110, like this embodiment, has the ground area 3, the stress $P_1$ acting on the center of the contact area 31 is given by $$P_1^3 = 3/(2 \times \pi^3) \times R^{-2} \times ((1-\nu^2)/E)^{-2} \times f \quad (2)$$

From Eqs. (1) and (2), it is found that $P_1/P_0$ is 0.63, and thus the ground area 3 contributes to an approximately 37% reduction in stress acting on the first and second porcelain insulators 11 and 12.

The ground area 3 may alternatively be formed only on the top end surface 120 of the second porcelain insulator 12. This structure also offers the same beneficial effects as described above.

We performed tests on samples of gas sensors to measure the mechanical strength of the first porcelain insulator 11 or the second porcelain insulator 12 which withstands applied loads.

Figure 8:
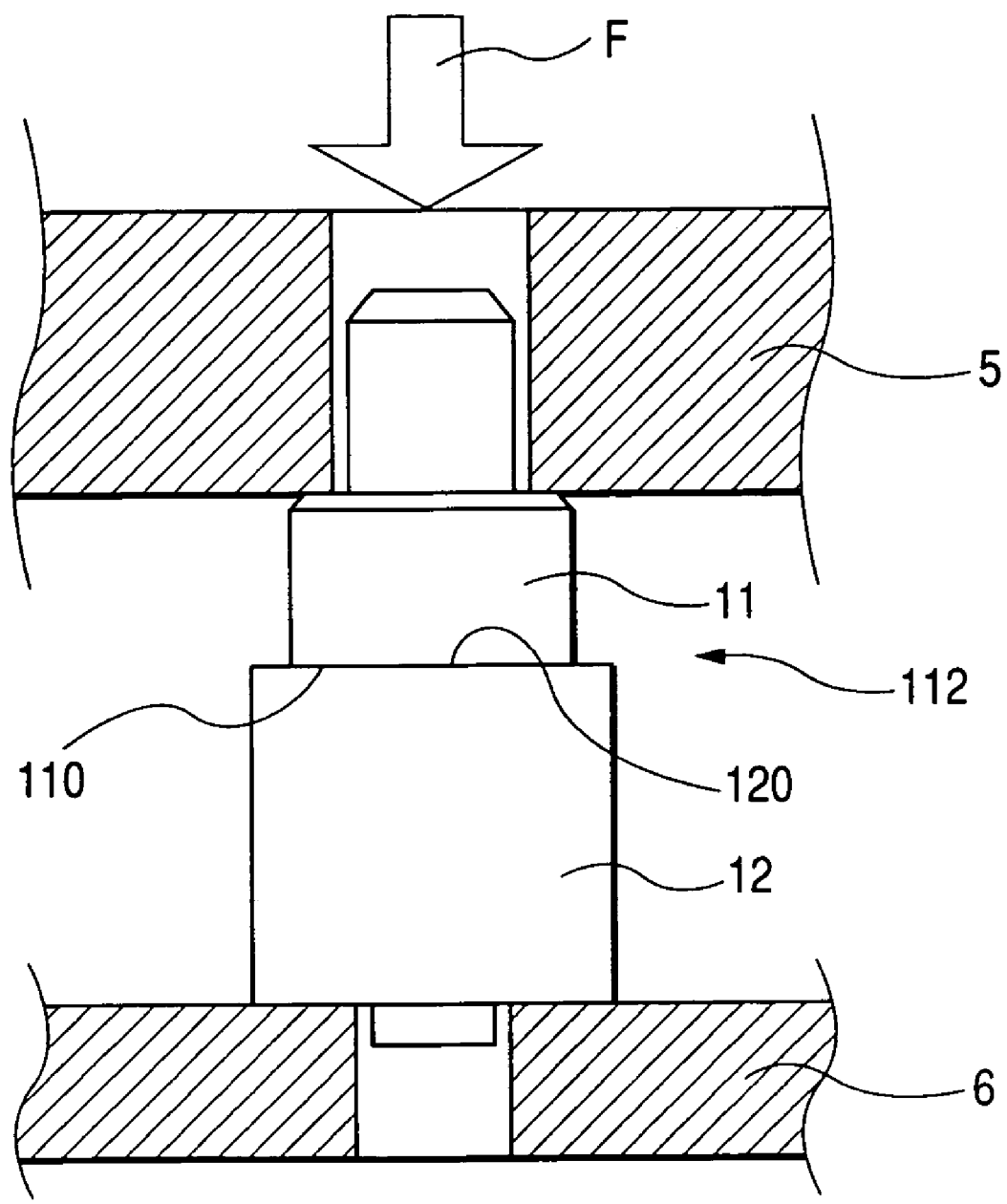
FIG. 8 is a partial sectional view which shows a test device used to measure the mechanical strength of a first porcelain insulator or a second porcelain insulator of gas sensor samples.

FIG. 8 illustrates a test device used to measure the strength of the first porcelain insulator 11 or the second porcelain insulator 12 of each of the samples.

We prepared a total of the eighty samples of the gas sensors equipped the first and second porcelain insulators 11 and 12. Twenty of them do not have the ground areas 3 both on the first and second porcelain insulators 11 and 12 and will be referred to here as comparative test samples. Twenty of them have, like the second embodiment, the ground area 3 formed only on the base end surface 110 of the first porcelain insulator 11 and will be referred to here as test sample No. 1. Twenty of them have the ground area 3 formed only on the top end surface 120 of the second porcelain insulator 12 and will be referred to here as test sample No. 2. The others have, like the first embodiment, the ground area 3 formed both on the base end surface 110 of the first porcelain insulator 11 and on the top end surface 120 of the second porcelain insulator 12 and will be referred to here as test sample No. 3.

Each of the tests was achieved by mounting the second porcelain insulator 12 on a base table 6 with the base end thereof facing downward, placing the first porcelain insulator 11 on the second porcelain insulator 12 in abutment of the base end surface 110 with the top end surface 120, fitting a press head 5 on the first porcelain insulator 11 from the top thereof, applying a physical load F to the press head 5, increasing the load F gradually, and measuring the value of the load F upon breakage of or formation of cracks in the first porcelain insulator 11 or the second porcelain insulator 12.

FIGS. 9(a) to 9(d) are graphs representing results of the tests. The vertical axis indicates the load F. The horizontal axis indicates the number of the test samples broken or cracked. The breakage of or cracks in the first and second porcelain insulators 11 and 12 were observed using the staining method.

The graphs of FIGS. 9(a) to 9(d) show that the number of the test samples No. 1 and No. 2 in which the first porcelain insulator 11 or the second porcelain insulator 12 are broken or cracked is smaller than that of the comparative test samples in a lower load range. Specifically, it is found that the ground area 3 formed on either of the base end surface 110 of the first porcelain insulator 11 or the top end surface 120 of the second porcelain insulator 12 serves to enhance the resistance to the breakage thereof. The graph of FIG. 9(d) also shows that such a resistance is most increased in the case where the ground areas 3 are formed both on the base end surface 110 of the first porcelain insulator 11 and the top end surface 120 of the second porcelain insulator 12.

We also performed tests to measure the mechanical strength of the first porcelain insulator 11 or the second porcelain insulator 12 which withstands applied loads in the same manner as discussed above.

Figure 10A:
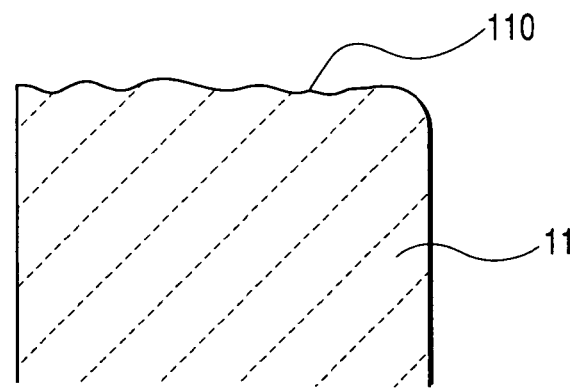
FIGS. 10($a$), 10($b$), and 10($c$) are partially sectional views which show a base end surface of a first porcelain insulator of gas sensor samples used in measuring the mechanical strength of a first porcelain insulator or a second porcelain insulator.
Figure 10B:
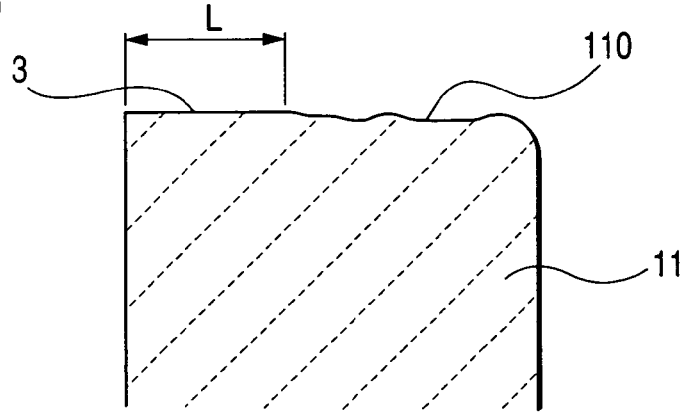
Figure 10C:
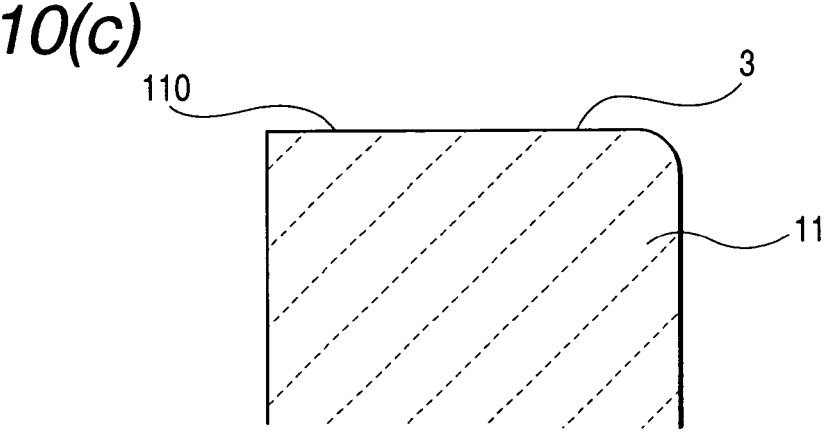

We prepared a total of the eighty samples of the gas sensors equipped the first and second porcelain insulators 11 and 12. All the samples do not have the ground area 3 on the top end surface 120 of the second porcelain insulator 12. Twenty of the samples, as illustrated in FIG. 10(a), have the first porcelain insulator 11 not ground and will be referred to here as comparative test samples. Twenty of the samples, as illustrated in FIG. 10(b), have the ground area 3 formed over a distance L of 0.15 mm to 0.5 mm (i.e., 0.15 mm$\leq$L<0.5 mm) on the base end surface 110 of the first porcelain insulator 11 in the radius direction thereof and will be referred to here as test sample No. 1. Twenty of the samples have the ground area 3 formed over a distance L of 0.5 mm to 1.0 mm (i.e., 0.5 mm$\leq$L$\leq$1.0 mm) on the base end surface 110 of the first porcelain insulator 11 in the radius direction thereof and will be referred to here as test sample No. 2. The others, as illustrated in FIG. 10(c), have the ground area 3 formed over the whole of the base end surface 100 of the first porcelain insulator 11 and will be referred to here as test sample No. 3. Note that FIGS. 10(a) and 10(b) enlarge the undulations on the base end surface 110 for ease of visibility.

FIGS. 11(a) to 11(d) are graphs representing results of the tests. The graph show that the number of the test samples No. 1, No. 2, and No. 3 in which the ground area 3 is formed on the base end surface 110 of the first porcelain insulator 11, and the first porcelain insulator 11 or the second porcelain insulator 12 is broken or cracked is smaller than that of the comparative test sample in a lower load range.

The graphs of FIGS. 11(b) to 11(d) show that the greater the distance L, the smaller the number of the test samples in which the first porcelain insulator 11 or the second porcelain insulator 12 are broken or cracked in the lower load range. Specifically, it is found that the greater the size of the ground area 3, the greater will be the resistance of the first porcelain insulator 11 or the second porcelain insulator 12 to the breakage.

The graphs of FIGS. 11(c) and 11(d) show that the ground area 3 formed over the distance L≧0.5 mm on the base end surface 110 of the first porcelain insulator attains substantially the same effects as those in the case where the ground area 3 is formed on the whole of the base end surface 110. It is found that the ground area 3 needs not necessarily be formed over the whole of the base end surface 110, but may occupy a distance of at least 0.5 mm on the base end surface 110 in the radius direction thereof.

We also measured the flatness of the base end surface 110 of the first porcelain insulator 11 and the top end surface 120 of the second porcelain insulator 12 before ground. This measurement was achieved by tracing the profile of the undulations on the base end surface 110 and the top end surface 120 before ground using a contact needle surface roughness tester.

Figure 12A:
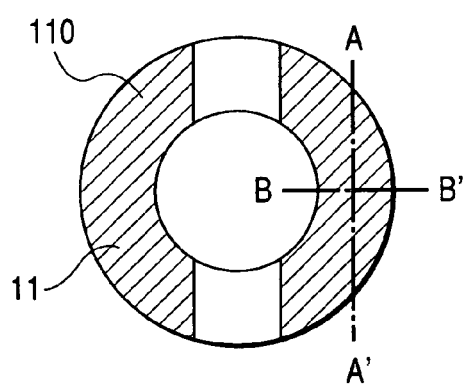
FIG. 12($a$) is a plane view which represents directions in which the flatness of a base end surface of a first porcelain insulator was measured experimentally.
Figure 12B:
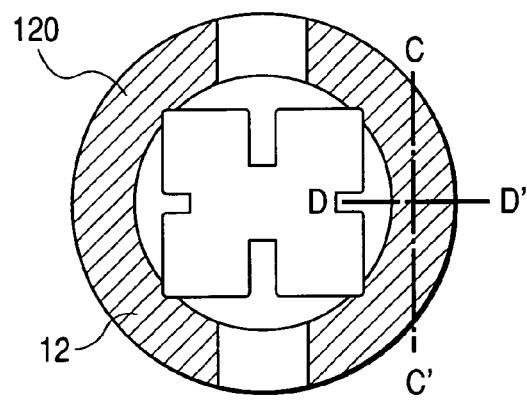

FIG. 12(a) represents directions of measurements of the flatness of the base end surface 110 of the first porcelain insulator 11. FIG. 12(b) represents directions of measurements of the flatness of the top end surface 120 of the second porcelain insulator 12. FIGS. 13(a) to 16(b) are graphs which represent results of the measurements. In each graph, one vertical scale indicates 5 μm, and one horizontal scale indicates 0.5 mm.

Figure 13A:
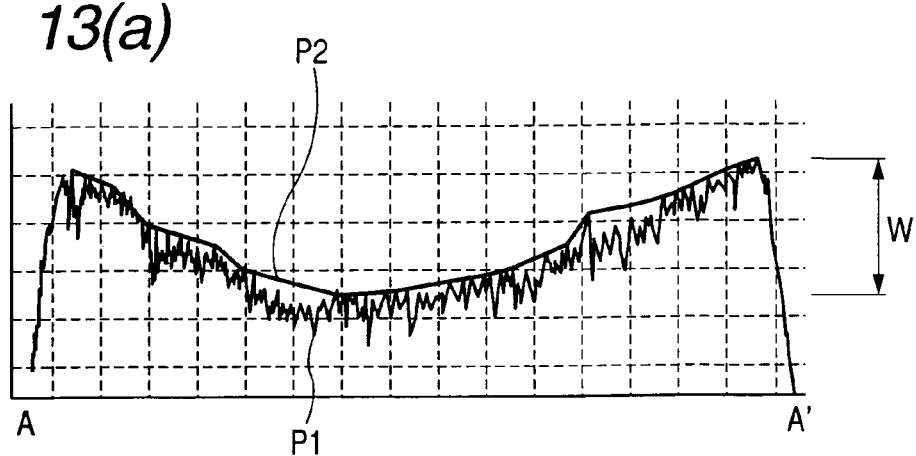
FIG. 13($a$) is a graph which shows the profile of a base end surface of a first porcelain insulator before ground, as measured along the line A-A' in FIG. 12($a$)
Figure 13B:
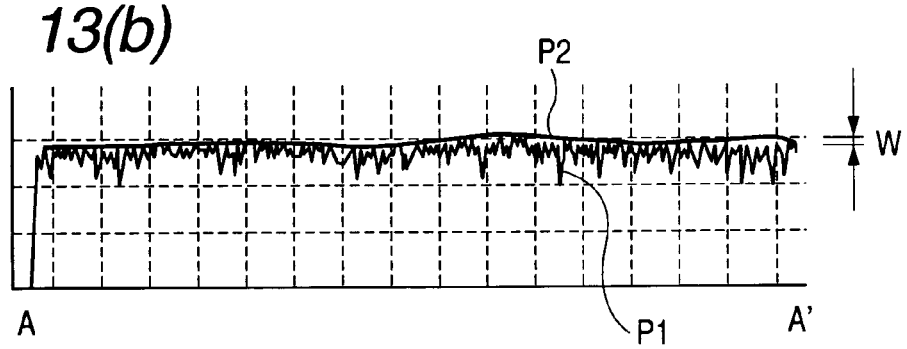
Figure 14A:
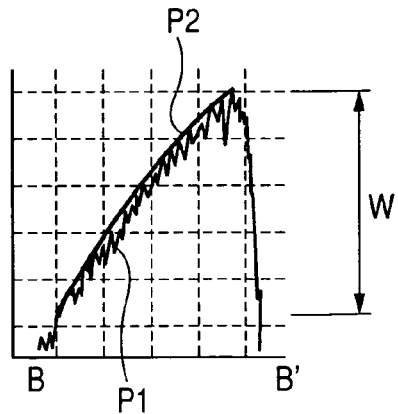
FIG. 14($a$) is a graph which shows the profile of a base end surface of a first porcelain insulator before ground, as measured along the line B-B' in FIG. 12($a$)
Figure 14B:
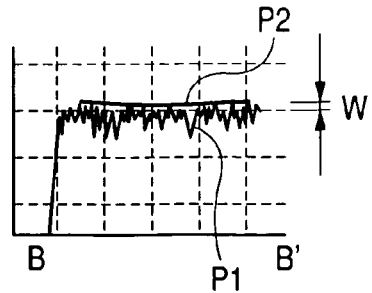
Figure 15A:
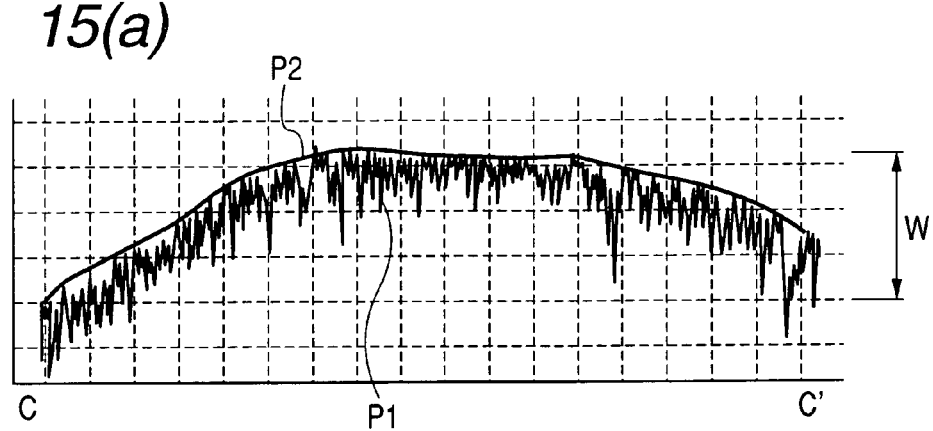
FIG. 15($a$) is a graph which shows the profile of a top end surface of a second porcelain insulator before ground, as measured along the line C-C' in FIG. 12($b$)
Figure 15B:
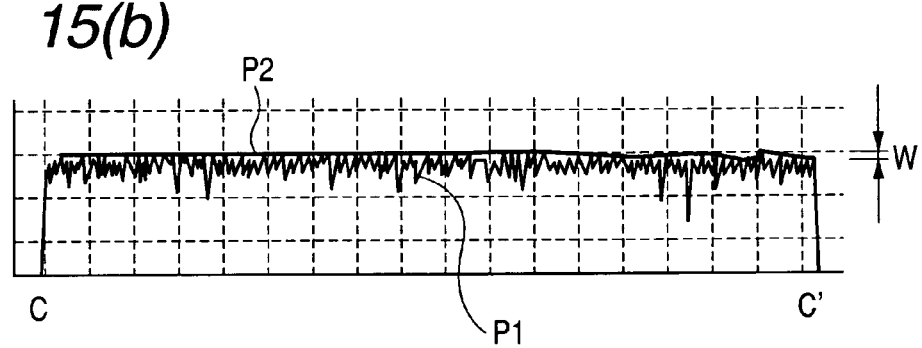
Figure 16A:
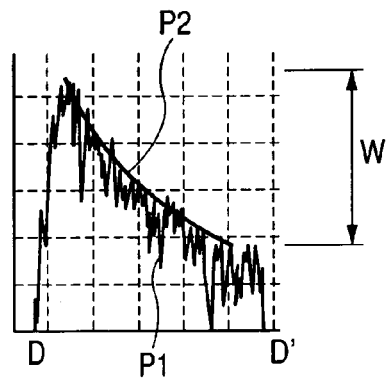
FIG. 16($a$) is a graph which shows the profile of a top end surface of a second porcelain insulator before ground, as measured along the line D-D' in FIG. 12($b$)
Figure 16B:
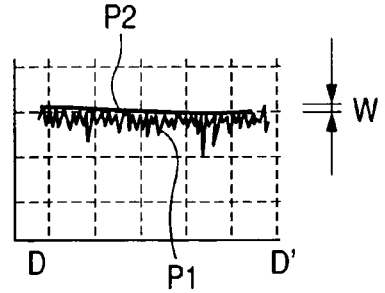
Figure 17:
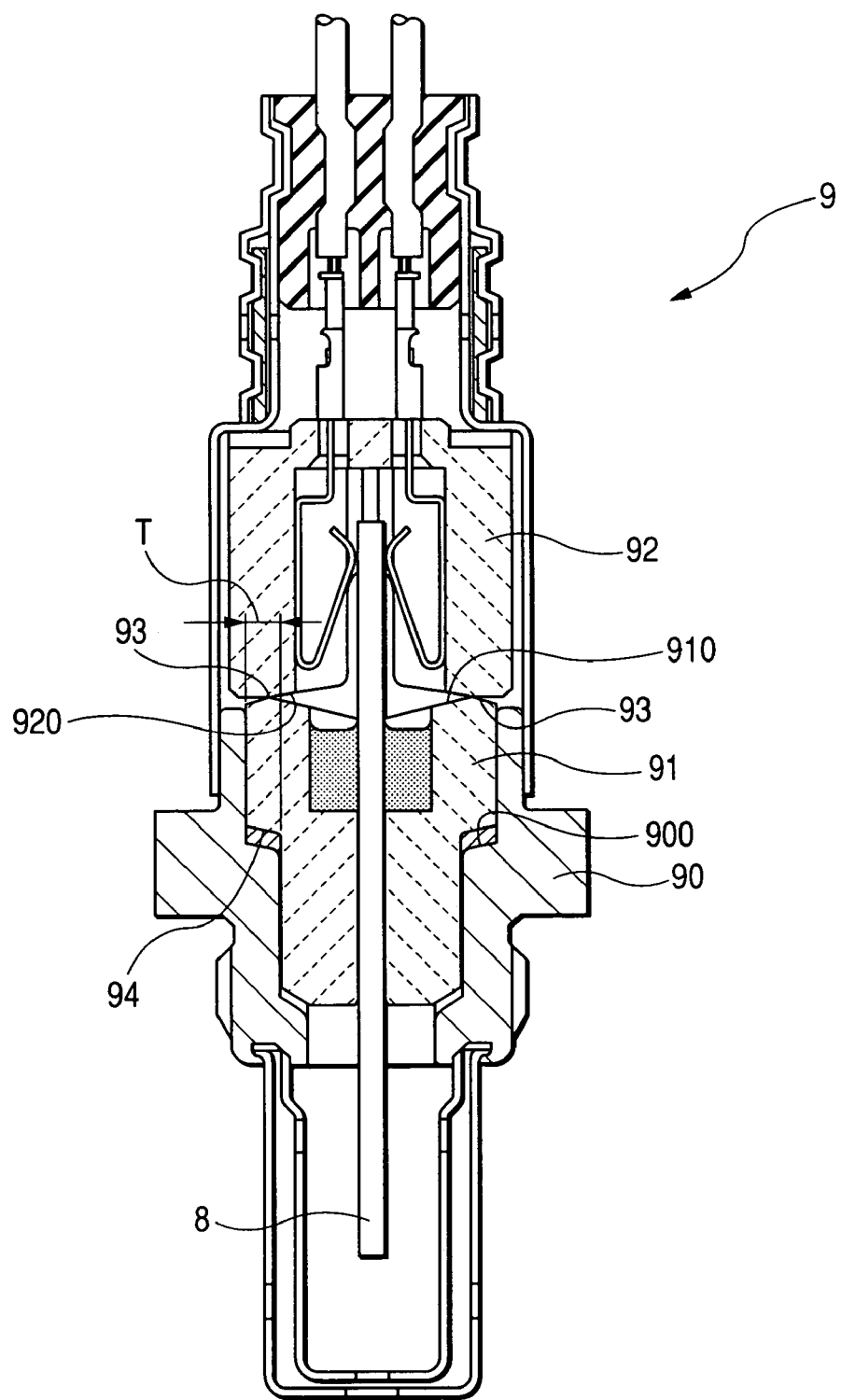
FIG. 17 is a longitudinal sectional view which shows a conventional gas sensor.

FIG. 13(a) shows the profile of the base end surface 110 of the first porcelain insulator 11 before ground, as measured along the line A-A' in FIG. 12(a). FIG. 13(b) shows the profile of the base end surface 110 of the first porcelain insulator 11 after ground, as measured along the line A-A' in FIG. 12(a). FIG. 14(a) shows the profile of the base end surface 110 of the first porcelain insulator 11 before ground, as measured along the line B-B' in FIG. 12(a). FIG. 14(b) show the profile of the base end surface 110 of the first porcelain insulator 11 after ground, as measured along the line B-B' in FIG. 12(a). FIG. 15(a) shows the profile of the top end surface 120 of the second porcelain insulator 12 before ground, as measured along the line C-C' in FIG. 12(b). FIG. 15(b) shows the profile of the top end surface 120 of the second porcelain insulator 12 after ground, as measured along the line C-C' in FIG. 12(b). FIG. 16(a) shows the profile of the top end surface 120 of the second porcelain insulator 12 before ground, as measured along the line D-D' in FIG. 12(b). FIG. 16(b) shows the profile of the top end surface 120 of the second porcelain insulator 12 after ground, as measured along the line D-D' in FIG. 12(b). In each graph, the thin line P1 indicates the profile of undulations. The thick line P2 indicates an envelope curve defined by connecting peaks of undulations in a sequence of small zones to which the base end surface 110 or the top end surface 120 are subdivided in unit of 0.5 mm along the line A-A', B-B', C-C', or D-D'.

FIGS. 12(a), 12(b), 13(a), 14(a), 15(a), and 16(a) show that in the absence of the ground areas 3, there are great undulations on the base end surface 110 of the porcelain insulator 11 and on the top end surface 120 of the second porcelain insulator 12, and the amplitude of the undulations on the top end surface 120 increases as approaching the longitudinal center of the gas sensor 1.

FIGS. 13(a) to 16(b) show that before the base end surface 110 and the top end surface 120 are ground, amplitudes W of envelope curves of the undulations lie within a rang of approximately 15 μm to 25 μm, and after they are ground, the amplitudes W fall within a range of 5 μm or less.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor comprising:
   a hollow cylindrical housing;
   a sensor element including a sensing portion and a base portion, said sensing portion working to produce a signal as a function of concentration of a target component of gases;
   a first porcelain insulator having a top end surface and a base end surface opposed to the top end surface, said first porcelain insulator being installed in said housing and through and having said sensor element pass therethrough to expose the sensing portion to the gases outside the top end surface of said housing;
   a second porcelain insulator having a top end surface and a base end surface opposed to the top end surface, said second porcelain insulator being aligned with said first porcelain insulator in abutment of the top end surface thereof with the base end surface of said first porcelain insulator; and
   a ground flat area formed on at least one of the base end surface of said first porcelain insulator and the top end surface of said second porcelain insulator to define an area of contact between the base end surface of said first porcelain insulator and the top end surface of said second porcelain insulator, the ground flat area being formed using one of a lapping machine and a grinding machine, whereby there is an increase in an area of contact between the base end surface of said first porcelain insulator and the top end surface of the second porcelain insulator at said abutment, thereby minimizing a concentration of stress on said area of contact.

2. A gas sensor as set forth in claim 1, wherein each of the base end surface of said first porcelain insulator and the top end surface of said second porcelain insulator has said ground flat area.

3. A gas sensor as set forth in claim 1, wherein each of said first and second porcelain insulator is made of a cylindrical member, and wherein said ground flat area occupies a distance of 0.5 mm or more on the one of the base end surface of said first porcelain insulator and the top end surface of said second porcelain insulator in a radius direction of the one.

4. A gas sensor as set forth in claim 1, wherein said ground flat area is so formed that an amplitude of an envelope curve defined by connecting peaks of undulations in a sequence of small zones to which a surface of said ground flat area is divided in unit of 0.5 mm in a selected direction lies within a range of 5 μm or less.

5. A gas sensor as set forth in claim 1, wherein said first porcelain insulator has a recess formed in the base end surface thereof, said second porcelain insulator having a protrusion formed on the top end surface thereof, and wherein said first and second porcelain insulators are placed in engagement of the recess in the base end surface of said first porcelain insulator with the protrusion on the top end surface of said second porcelain insulator.

6. A gas sensor as set forth in claim 1, wherein each of the base end surface of said first porcelain insulator and the top end surface of said second porcelain insulator has said ground flat area formed using the one of the lapping machine and the grinding machine.

7. A gas sensor comprising:
a hollow cylindrical housing;
a sensor element including a sensing portion and a base portion, said sensing portion working to produce a signal as a function of concentration of a target component of gases;
a first porcelain insulator having a top end surface and a base end surface opposed to the top end surface, said first porcelain insulator being installed in said housing and through and having said sensor element pass therethrough to expose the sensing portion to the gases outside the top end surface of said housing;
a second porcelain insulator having a top end surface and a base end surface opposed to the top end surface, said second porcelain insulator being aligned with said first porcelain insulator in abutment of the top end surface thereof with the base end surface of said first porcelain insulator; and
a ground flat area formed on at least one of the base end surface of said first porcelain insulator and the top end surface of said second porcelain insulator to define an area of contact between the base end surface of said first porcelain insulator and the top end surface of said second porcelain insulator,
wherein each of said first and second porcelain insulator is made of a cylindrical member, and wherein said ground flat area occupies a distance of 0.5 mm or more on the one of the base end surface of said first porcelain insulator and the top end surface of said second porcelain insulator in a radius direction of the one.

8. A gas sensor comprising:
a hollow cylindrical housing;
a sensor element including a sensing portion and a base portion, said sensing portion working to produce a signal as a function of concentration of a target component of gases;
a first porcelain insulator having a top end surface and a base end surface opposed to the top end surface, said first porcelain insulator being installed in said housing and through and having said sensor element pass therethrough to expose the sensing portion to the gases outside the top end surface of said housing;
a second porcelain insulator having a top end surface and a base end surface opposed to the top end surface, said second porcelain insulator being aligned with said first porcelain insulator in abutment of the top end surface thereof with the base end surface of said first porcelain insulator; and
a ground flat area formed on at least one of the base end surface of said first porcelain insulator and the top end surface of said second porcelain insulator to define an area of contact between the base end surface of said first porcelain insulator and the top end surface of said second porcelain insulator,
wherein said ground flat area is so formed that an amplitude of an envelope curve defined by connecting peaks of undulations in a sequence of small zones to which a surface of said ground flat area is divided in unit of 0.5 mm in a selected direction lies within a range of 5 µm or less.

* * * * *